United States Patent
Toyokawa et al.

(10) Patent No.: US 8,804,911 B2
(45) Date of Patent: Aug. 12, 2014

(54) NONDESTRUCTIVE INSPECTION SYSTEM USING NUCLEAR RESONANCE FLUORESCENCE

(75) Inventors: Hiroyuki Toyokawa, Ibaraki (JP); Ryoichi Hajima, Ibaraki (JP); Takehito Hayakawa, Kyoto (JP); Toshiyuki Shizuma, Kyoto (JP); Nobuhiro Kikuzawa, Ibaraki (JP); Hideaki Ohgaki, Kyoto (JP)

(73) Assignees: National Institute of Advanced Industrial Science and Technology, Tokyo (JP); Japan Atomic Energy Agency, Ibaraki (JP); Kyoto University, Kyoto (JP)

( * ) Notice: Subject to any disclaimer, the term of this patent is extended or adjusted under 35 U.S.C. 154(b) by 399 days.

(21) Appl. No.: 13/254,835

(22) PCT Filed: Mar. 4, 2010

(86) PCT No.: PCT/JP2010/053560
§ 371 (c)(1), (2), (4) Date: Sep. 2, 2011

(87) PCT Pub. No.: WO2010/101221
PCT Pub. Date: Sep. 10, 2010

(65) Prior Publication Data
US 2012/0002783 A1 Jan. 5, 2012

(30) Foreign Application Priority Data
Mar. 5, 2009 (JP) ................. 2009-051497

(51) Int. Cl.
*H05G 2/00* (2006.01)
*G21K 5/00* (2006.01)
*G21K 5/04* (2006.01)
*G21K 5/08* (2006.01)
*G21K 5/10* (2006.01)

(52) U.S. Cl.
USPC .................. 378/119; 378/64; 378/68; 378/69

(58) Field of Classification Search
USPC ............................ 378/44, 45, 119, 64, 68, 69
See application file for complete search history.

(56) References Cited

U.S. PATENT DOCUMENTS 3,171,961 A * 3/1965 Yule ............................... 376/166
5,115,459 A * 5/1992 Bertozzi ......................... 378/88
(Continued)

FOREIGN PATENT DOCUMENTS

JP 2006-318746 A 11/2006
JP 2008-506124 A 2/2008
(Continued)

OTHER PUBLICATIONS

J. Pruet et al., "Detecting clandestine material with nuclear resonance fluorescence," Journal of Applied Physics 99, 123102 (20006).*
(Continued)

Primary Examiner — Allen C. Ho
(74) Attorney, Agent, or Firm — Perkins Coie LLP (57) ABSTRACT

Isotope identification imaging of nuclear fuel material or explosives concealed in a drum or container in which nuclear reactor fuel or radioactive waste are sealed is realized while ensuring high precision, high reliability, and safety. A sample 31 is irradiated with laser Compton photon beams 21 and 22 generated by a collision between an electron beam 12 and polarized laser light 16 and 20. An isotope in the sample is identified using nuclear resonance fluorescence, and the spatial distribution thereof is imaged. In so doing, a nuclear level of an isotope whose emission direction of nuclear resonance fluorescence is dependent on the planes of polarization of the incident LCS photon beams is used.

19 Claims, 8 Drawing Sheets

(56) References Cited

U.S. PATENT DOCUMENTS

| | | | |
|---|---|---|---|
| 5,274,689 A * | 12/1993 | Palathingal et al. | 378/119 |
| 5,293,414 A * | 3/1994 | Ettinger et al. | 378/88 |
| 5,420,905 A * | 5/1995 | Bertozzi | 378/88 |
| 5,825,847 A * | 10/1998 | Ruth et al. | 378/119 |
| 7,120,226 B2 * | 10/2006 | Ledoux et al. | 378/57 |
| 7,286,638 B2 * | 10/2007 | Ledoux et al. | 378/88 |
| 7,356,115 B2 * | 4/2008 | Ford et al. | 378/57 |
| 7,564,241 B2 * | 7/2009 | Barty et al. | 324/304 |
| 7,949,097 B2 * | 5/2011 | Bertozzi et al. | 378/88 |
| 7,994,472 B2 * | 8/2011 | Plettner et al. | 250/251 |
| 8,023,618 B2 * | 9/2011 | Bertozzi et al. | 378/86 |
| 8,180,019 B2 * | 5/2012 | Bertozzi et al. | 378/57 |
| 8,369,480 B2 * | 2/2013 | Barty | 378/57 |
| 2009/0252296 A1 | 10/2009 | Nose et al. | |

FOREIGN PATENT DOCUMENTS

| | | | | |
|---|---|---|---|---|
| JP | 2012032220 A * | 2/2012 | | G01N 23/22 |
| WO | 2006-010056 A2 | 1/2006 | | |

OTHER PUBLICATIONS

Ryoichi Hajima et al., "Proposal of Nondestructive Radionuclide Assay Using a High-Flux Gamma-Ray Source and Nuclear Resonance Fluorescence," Journal of Nuclear Science and Technology, vol. 45, No. 5, p. 441-451 (2008).*

International Search Report and Written Opinion dated May 18, 2010 for Application No. PCT/JP2010/053560, filed Mar. 4, 2010 (4 pages).

Ogaki, H., et al., "Material Identification by Nuclear Resonance Fluorescence Method" Atomic Energy Society of Japan 2008 Fall Meeting, I31:495, Aug. 2008 (4 pages).

Hajima, R., et al., "Proposal of Nondestructive Radionuclide Assay Using a High-Flux Gamma-Ray Source and Nuclear Resonance Fluorescence" Journal of Nuclear Science and Technology, 45(5):441-451, May 2008 (12 pages).

* cited by examiner

| LEGEND |
|---|
| 36: drive part |
| 37: control processing part |
| 38: monitor |

NONDESTRUCTIVE INSPECTION SYSTEM USING NUCLEAR RESONANCE FLUORESCENCE

TECHNICAL FIELD

The present invention relates to a nondestructive inspection system using nuclear resonance fluorescence.

BACKGROUND ART

Various isotopes including fissionable materials are contained in fuel rods and radioactive waste that are handled in nuclear fuel cycles for nuclear power generation. Inspecting these in a nondestructive manner and visualizing their spatial distribution are important in realizing safe and efficient nuclear fuel cycles. By way of example, with respect to cesium, there is Cs-133, which is a stable isotope with an atomic mass number of 133, and there is Cs-137, which is a radioactive nuclide with an atomic mass number of 137, where the handling of the latter is strictly controlled by law. In radioactive waste treatment, by quickly identifying them, costs associated with underground disposal can be reduced dramatically. The realization of a technique for identifying isotopes and visualizing the spatial distribution thereof is therefore strongly desired.

In addition, in transporting nuclear fuel materials, measuring, in a nondestructive manner and from outside of a container, fissionable materials, such as uranium, etc., nuclear fuel materials, explosives, and materials from which they are made concealed inside the container is extremely important for purposes of strictly restricting/controlling transportation of nuclear materials, in preventing terrorism, etc., involving explosives, and in realizing a safe and secure society.

Currently, at some nuclear fuel cycle facilities, seaports, airports, etc., X-ray transmission image-based internal geometry measurement and nondestructive inspection of fissionable materials, nuclear fuel materials, explosives, etc., are performed using large-scale X-ray inspection equipment that inspects fuel rods and containers in their entirety, or prompt gamma ray analyzers that use a neutron generator, etc. In X-ray inspection, a hard high-energy bremsstrahlung X-ray is used, and while there is an advantage in that a clear transmission image is obtained, the material cannot be identified. Prompt gamma ray analysis by way of neutron radiation allows for material identification and isotope identification, but has poor spatial resolution, and its spatial resolution is insufficient for interior visualization. The term material identification as used herein refers to element identification, that is, to the identification of atoms. This may be done by observing the electron state around the nucleus, and may be observed with relative ease by means of X-rays, etc. The term isotope identification refers to the identification of an isotope, that is, of a nucleus with a different number of neutrons, with respect to the protons and neutrons contained in the nucleus, and may be observed by detecting gamma rays.

Figure 1:
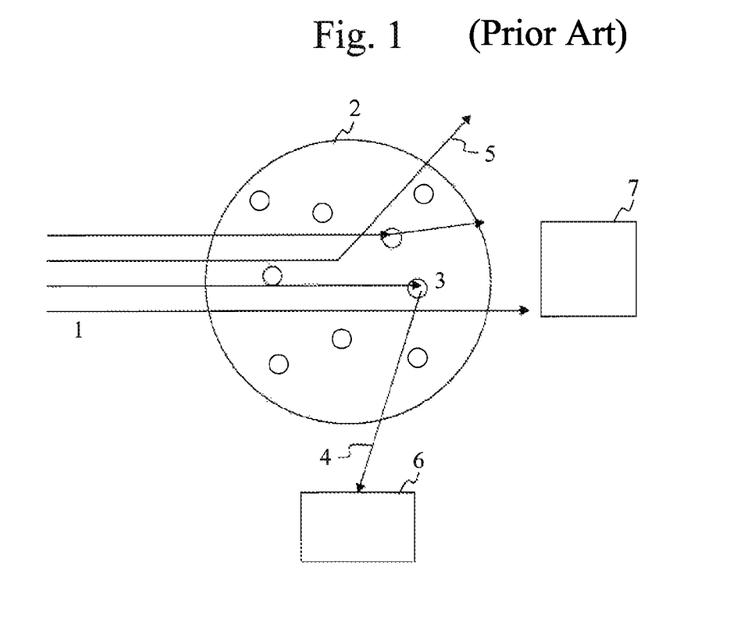
FIG. 1 is a diagram illustrating an isotope detection method using NRF.

With respect to material inspection of the interiors of import container cargos and suit cases, there is proposed an isotope identification method based on nuclear resonance fluorescence (NRF) using bremsstrahlung X-rays (Patent Document 1). The nucleus of an isotope has, depending on the number of protons and neutrons, which are constituent elements thereof, a natural frequency (excitation level). When the isotope is irradiated with a photon having an energy that matches this frequency, the isotope absorbs the photon, and a fluorescent photon is thereafter generated upon deexcitation, and this is referred to as NRF. Isotope identification may be carried out by observing NRF gamma rays with a radiation detector. Since NRF gamma rays have an energy of several MeV and are capable of passing through an iron plate of approximately 10 mm, isotope identification for and the spatial distribution of a material sealed inside a container, etc., may be measured in a nondestructive manner. The concept of the method is shown in FIG. 1.

A sample 2 is irradiated with photon beams 1 of X-rays, photons, etc. An isotope 3 of interest is contained in the sample 2. It is noted that the sample 2 may be shielded in some cases, however the shield is omitted here. The isotope 3 absorbs the photon beams 1, and emits an NRF gamma ray 4 which is detected by a radiation detector 6. The other photons are scattered by the other atoms within the sample to become scattered X-rays 5, and either exit the system or are detected by the radiation detector 6. A portion of the photon beams 1 that has been transmitted is measured at a photon intensity monitor 7. By scanning the photon beams 1 or by moving the sample 2, the spatial distribution of isotopes is measured.

With respect to the above-mentioned inspection, analysis, or treatment process, there is proposed a method in which quasi-monochromatic photons are generated through laser-Compton scattering (LCS, later discussed) instead of bremsstrahlung X-rays, and in which these are used for isotope detection. It is possible to generate LCS photons in the photon range of several MeV by irradiating a high-energy electron beam, which is generated by an electron accelerator, etc., with high-intensity laser.

As in ordinary Compton scattering, LCS is an interaction between electrons and photons, but is characterized in that the energy of the electrons is high, and that laser is used as photons. Photons generated by this method have the following characteristics: the photons are emitted within an extremely narrow solid angle and have high directionality comparable to synchrotron radiation; the photons may be made quasi-monochromatic by means of a collimator while at the same time reducing the energy spread (making them quasi-monochromatic) (Equation (1)) since there is a correlation between scattering angles of photons and energy; LCS photons with a high degree of polarization may be obtained since the polarization of the laser is preserved as is in the scattered photons (Equation (6), later discussed); and so forth.

Figure 2:
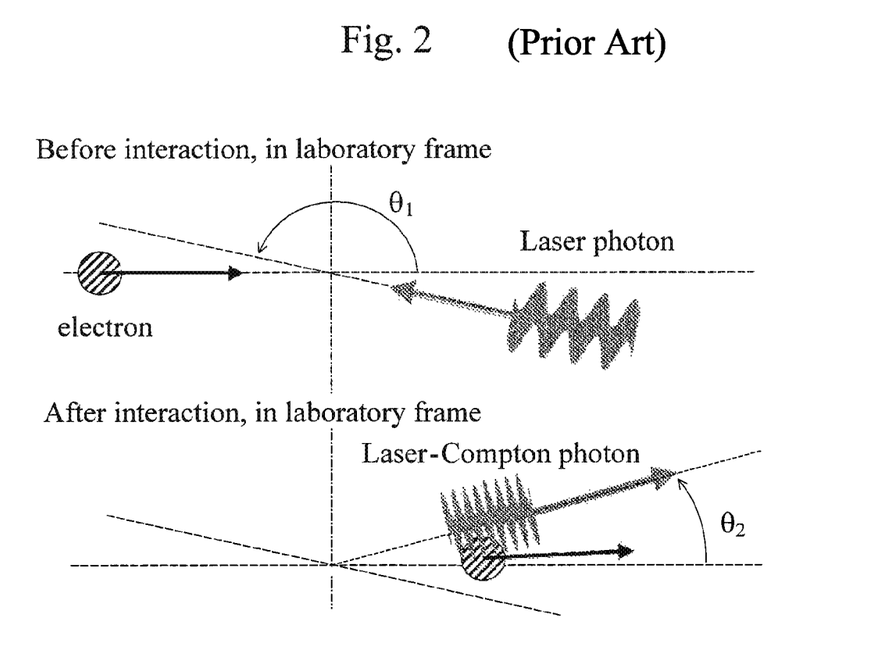
FIG. 2 is a diagram illustrating a dynamical system of laser Compton scattering.

The principles of LCS are represented in FIG. 2, and the relationship between energy $E_\gamma$ of LCS photons and energies of electrons and laser light through Equation (1). In Equation (1), $E_e$ represents the energy of electrons, and $E_L$ the energy of laser light.

$$E_\gamma = \frac{E_L(1-\beta\cos[\theta_1])}{1-\beta\cos[\theta_2] + \frac{E_L(1-\cos[\theta_2-\theta_1])}{E_e}} \quad (1)$$

$$\text{where } \beta = \sqrt{1-\gamma^2}, \gamma = \frac{E_e}{0.511}$$

Figure 3:
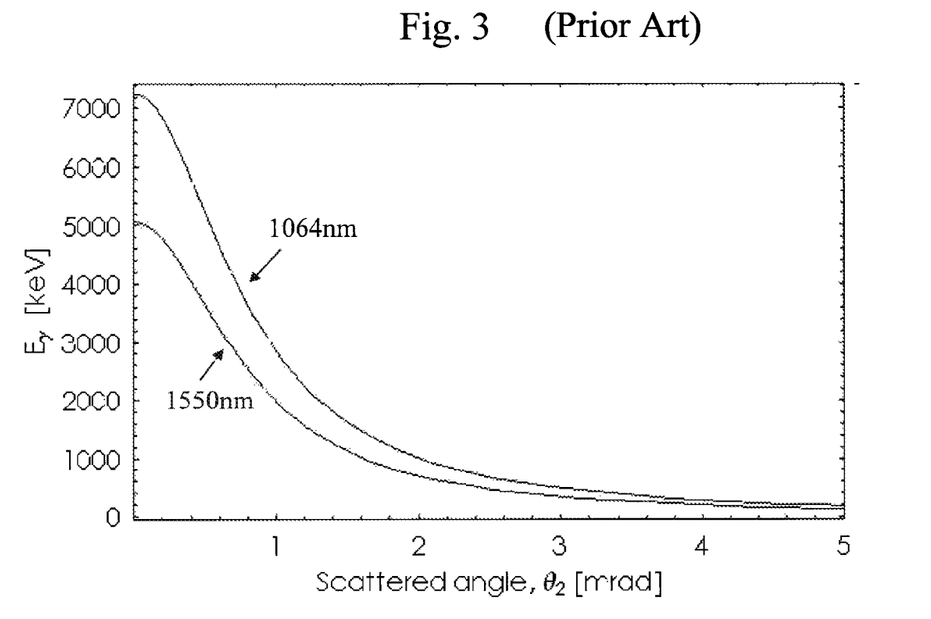
FIG. 3 is a chart showing the relationship between energy and scattering angle with respect to LCS photons obtained by irradiating electrons of an energy of 641 MeV with lasers with respective wavelengths of 1064 nm and 1550 nm.

The relationship between energy and scattering angle of LCS photons with respect to cases where electrons with an energy of 641 MeV are irradiated with lasers whose wavelengths are 1064 nm and 1550 nm is shown in FIG. 3. By restricting scattering angle $\theta_2$, it is possible to obtain photons with the desired energy and energy width. Specifically, the scattering angle is restricted by positioning a collimator in which a narrow hole is opened in lead, etc., along the beam axis. The energy width is ordinarily on the order of several %, and these are referred to as quasi-monochromatic photons.

An isotope's reaction cross-section $\sigma_D(E)$ is given by Equation (2). Resonance width $\Gamma$ is broadened due to Doppler broadening as given by Equation (3). However, the width of $\Delta$ is extremely narrow, and is ordinarily on the order several hundred meV.

$$\sigma_D(E) = \pi^{\frac{3}{2}} \left(\frac{\hbar c}{E}\right)^2 \frac{2I_1 + 1}{2I_0 + 1} \frac{\Gamma}{\Delta} \exp\left[-\left(\frac{E - E_{res}}{\Delta}\right)^2\right] \quad (2)$$

$$\Delta = E_{res} \sqrt{\frac{2kT_{\mathit{eff}}}{mc^2}} \quad (3)$$

Thus, in order to cause NRF efficiently, it is preferable that the excitation photon have a narrow energy spectrum that synchronizes with the natural frequency of the isotope. In the equations above, $\hbar$ represents the Planck constant/$2\pi$, c the speed of light, E the photon energy, I0 and I1 the total angular momenta in the ground state and the excited state, respectively, Eres the resonance energy, $\Gamma$ the resonance energy width, k the Boltzmann constant, Teff the effective temperature of a nucleus, and m the rest mass energy of an electron.

Since the energy spread of LCS photons can be narrowed to or below several %, it is possible to increase the signal-to-noise ratio (S/N) by reducing background noise (noise), which is advantageous to the method using bremsstrahlung X-rays. Thus, measuring methods that employ an LCS photon beam are superior in many aspects, such as precision, time, reliability, safety, etc., over cases where a bremsstrahlung X-ray is used.

In Non-Patent Document 1, there is proposed a method that uses LCS photons in an isotope identification method employing NRF. In Non-Patent Document 2, there is reported a method in which an Energy Recovery Linac (ERL), which is a next-generation electron accelerator, is combined with a state of the art high-power mode-locked fiber laser and a super cavity that accumulates pulsed laser, thereby generating LCS photons that are far more intense (approximately $10^8$ times so) than existing LCS photons. It is indicated that the abundance of long-lived nuclides within radioactive waste can thus be detected in a few seconds. Non-Patent Documents 3 and 4 contain reports regarding the detection of an NRF gamma ray with an energy of 5512 keV generated from lead-208, which is an isotope of lead, and imaging based thereon, as well as the detection of a 4439 keV NRF gamma ray from carbon-12, and material identification based thereon. The lead-208 sample was carefully concealed within an iron box with a thickness of 1.5 cm.

Figure 4:
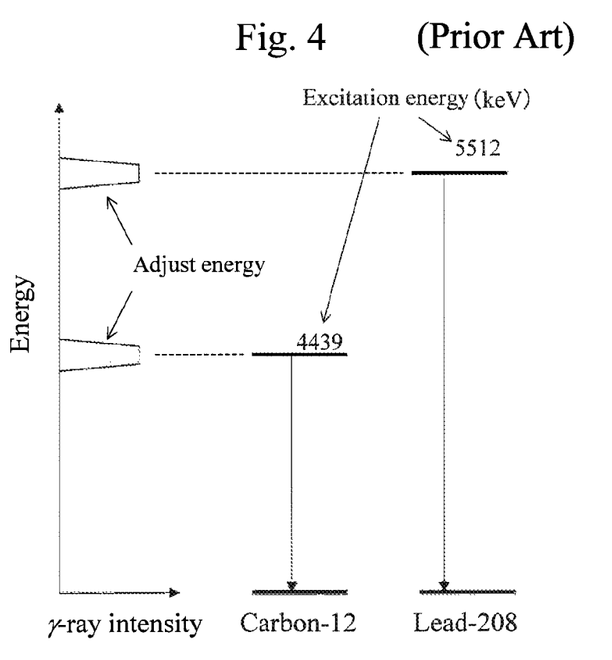
FIG. 4 is a diagram illustrating an isotope measuring method based on NRF gamma ray detection using LCS photon beams, where carbon-12 and lead-208 are provided as examples.

The nuclear excitation levels of carbon-12 and lead-208 are shown in FIG. 4. An LCS photon beam with a narrow energy width is used to excite nuclei. With the exception of hydrogen, there exists a unique excited state for each nucleus. When photons are emitted at the level (e.g., 5512 keV) of the nuclide to be measured (e.g., lead-208), the 5512 keV photons are absorbed by lead-208. In the process of cooling from the excited state, lead-208 emits NRF gamma rays that are equivalent to the excitation energy. By detecting these, it is possible to detect lead-208. LCS photon beams of the desired energy are generated by irradiating, with a laser with a wavelength of 1064 nm, 560 MeV electrons with respect to lead-208, and 510 MeV electrons with respect to carbon-12.

As a method for accurately analyzing elements contained within a substance, there is X-ray fluorescence analysis. Since X-ray fluorescence is low in energy, substances concealed inside containers cannot be measured. Further, since element analysis is carried out by utilizing the fact X-rays generated due to the structures of atoms, that is, due to electron transition (characteristic X-rays), represent states unique to the atoms, while elements may be identified, isotopes may not.

There is proposed a method in which a sample is irradiated with a high-energy gamma ray to induce a ($\gamma$, n) reaction with respect to the isotope of interest, thereby producing nuclear isomers, and in which isotope identification is carried out using the deexcitation gamma ray thereof (Patent Document 2).

PRIOR ART DOCUMENTS

Patent Documents

Patent Document 1: U.S. Pat. No. 7,286,638
Patent Document 2: JP 2004-219187 A
Patent Document 3: JP 2006-318746 A Non-Patent Documents Non-Patent Document 1: J. Pruet, D. P. McNabb, C. A. Hagmann, F. V. Hartemann and C. P. J. Barty, J. Appl. Phys. 99 (2006) 123102
Non-Patent Document 2: R. Hajima, T. Hayakawa, N. Kikuzawa, E. Minehara, J. Nucl. Sci. and Technol. Vol. 45, No. 5, pp. 441-451, 2008
Non-Patent Document 3: Nobuhiro Kikuzawa, Ryoichi Hajima, Takehito Hayakawa, Toshiyuki Shizuma, Eisuke Minehara, Hiroyuki Toyokawa, Hideaki Ohgaki: "Verifying the principles of a radioactive isotope detection technique by photonuclear resonant scattering using quasi-monochromatic $\gamma$-rays", 2008 Annual Meeting of the Atomic Energy Society of Japan
Non-Patent Document 4: Hideaki Ohgaki, Toshiteru Kii, Kai Masuda, Hiroyuki Toyokawa, Ryoichi Suzuki, Nobuhiro Kikuzawa, Toshiyuki Shizuma, Takehito Hayakawa, Ryoichi Hajima, Eisuke Minehara: "Material identification—light nucleus identification using nuclear resonant scattering by laser inverse Compton scattered $\gamma$-rays", 2008 Annual Meeting of the Atomic Energy Society of Japan

SUMMARY OF THE INVENTION

Problems to be Solved by the Invention

Imaging that utilizes prompt gamma rays by neutron radiation have the following problems in addition to its shortcoming of being poor in spatial resolution. Specifically, not only the substance within a container, but also the nuclei of the iron and lead with which the container is built are excited at the same time due to neutron radiation. The prompt gamma ray spectra consequently become extremely complex, which makes solving them within a short period extremely difficult. In addition, when neutrons are absorbed by the nuclei of uranium-233 or -235, plutonium-239, uranium-238, etc., nuclear fission could occur. In particular, uranium-233 and -235, and plutonium-239 pose a high risk of triggering a chain reaction. In addition, since the atomic number sometimes changes due to neutron radiation, there is also a problem in that it may turn into a substance that is different from the original substance (nuclear transmutation).

Since bremsstrahlung X-rays vary widely in wavelength, numerous levels of a plurality of isotope nuclei may be excited simultaneously. However, the energy width that contributes to NRF is extremely narrow and on the order of several hundred meV even with thermal Doppler broadening taken into account, and all X-rays with energies falling outside of that become noise, thereby giving rise to a problem which is that S/N becomes extremely small. Specifically, the fact that reliability with respect to measurement precision, quantifying capability, etc., is low, and the fact that measurement takes a long time are practical problems. In addition, when the electron energy is made to be equal to or higher than the neutron emission energy (generally around 8 MeV, with some variation depending on the nuclide), neutrons are emitted from the isotope to be measured, which causes numerous problems, such as safety, increased costs for installing shielding, and so forth. In particular, if a fissionable material is contained in the sample, there is a risk of nuclear fission being triggered. Therefore, using bremsstrahlung X-rays equal to or above the neutron emission energy is extremely dangerous and must be avoided at all costs. As the electron energy is lowered, the energy spectrum of bremsstrahlung X-rays as a whole shifts towards the low-energy side, and the neutron emission rate drops. In the low-energy region, large amounts of low-energy X-rays and characteristic X-rays are emitted due to atomic scattering. There is consequently a disadvantage in that NRF gamma rays to be measured become buried in noise and S/N becomes small. In particular, it has been difficult to detect important isotopes such as carbon-12, nitrogen-14, etc., whose excitation levels are at 4 to 5 MeV.

By collimating an LCS photon beam to a diameter of several mm, it is possible to narrow the energy width to or below several %. In Patent Document 1, Non-Patent Document 1 and Non-Patent Document 2 discussed above, it is mentioned that S/N is improved utilizing this method, while also shortening measurement time. However, with the methods presented in these documents, since only a narrow energy width can be excited, it is not possible to inspect a plurality of elemental ratios in one measurement.

In view of the above, a method of inferring the type of an explosive by measuring the abundance ratios and abundances of isotopes nondestructively and remotely is proposed.

By way of example, in naturally occurring carbon, 98.89% of carbon-12 ($^{12}$C) is contained, and 99.64% of nitrogen-14 ($^{14}$N) and 99.76% of oxygen-16 ($^{16}$O) are respectively contained in nitrogen and oxygen. As levels of these isotopes, carbon-12 (4439 keV), nitrogen-14 (4915 keV and 7029 keV), and oxygen-16 (6917 keV and 7117 keV) are used. As the levels above are spaced apart in energy, only a single level can be excited with conventional methods. Thus, there was a disadvantage in that, even if the abundance of carbon-12 were detected with high precision, it was impossible to tell whether it was from an explosive or from surrounding structures.

In other words, although there is a need to vary the LCS photon energy to measure different isotopes, because conventional methods only allow for excitation of a single level, the electron energy or laser wavelength had to be varied. With respect to LCS photons, since a laser and an electron beam are made to collide after being converged to a size of several tens of μm to 100 μm in diameter, yield would drop significantly if the electron orbit were to be off even slightly. Although it is not impossible to adjust the orbit of an electron beam with precision on the order of several tens of μm using existing techniques, it would require extensive measurement apparatus and extended periods of adjustment, thereby restricting implementation thereof to large-scale accelerators. When the energy of an electron beam is varied, the electron orbit varies, and it becomes difficult to generate LCS photon beams along the same axis, thereby precluding accurate visualization of the positions of isotopes.

The fact that extended periods are required for, in addition to such fine adjustments, fine adjustments of the position of the collimator positioned along the laser or beam axis is also a practical problem.

Means for Solving the Problems

A nondestructive inspection system of the present invention comprises: a plate that holds a sample; a plurality of radiation detectors positioned in predetermined directions relative to the sample held by the plate; a photon beam irradiation part that irradiates the sample held by the plate with a plurality of types of quasi-monochromatic photon beams having differing energies and whose planes of polarization are each controlled, the quasi-monochromatic photon beams being made to be coaxial; a drive part that relatively moves the plate and the photon beam irradiation part; a control processing part that controls the drive part and to which detection signals from the plurality of radiation detectors are inputted; and a display part, wherein the radiation detectors are positioned in directions that allow for detection of NRF gamma rays emitted from a nuclear level of an isotope within the sample in directions that are dependent on the planes of polarization of the quasi-monochromatic photon beams with which the sample is irradiated, wherein the control processing part identifies an isotope of interest that is present in a photon beam irradiated region in the sample based on the detection signals of the radiation detectors, and wherein a spatial distribution thereof is visualized and displayed on the display part. LCS photon beams are suitable for use as the plurality of types of quasi-monochromatic photon beams whose planes of polarization are each controlled. However, other photon beams having similar polarization characteristics and energy characteristics may also be used.

By way of example, the photon beam irradiation part utilizes laser Compton scattering to coaxially generate a plurality of LCS photon beams having a single energy or several energies and whose planes of polarization are each controlled. Specifically, the photon beam irradiation part comprises: an electron beam accelerator that generates an electron beam of a predetermined energy; a first laser light source that generates laser light of a first wavelength and having a first polarization; and a second laser light source that generates laser light of a second wavelength and having a second polarization, wherein the laser light of the first wavelength and the laser light of the second wavelength are made to collide with the electron beam at a first angle and as coaxial light. A first polarized LCS photon beam resulting from the laser light of the first wavelength and a second polarized LCS photon beam resulting from the laser light of the second wavelength, which are generated by laser Compton scattering, are then extracted via a collimator positioned in a second angular direction relative to the electron beam.

It is preferable that the first laser light source and the second laser light source be controlled by the control processing part and that they each generate pulsed light with a different time structure. The planes of polarization of the LCS photon beams may be made to be mutually parallel or perpendicular to the plane of polarization of one LCS photon beam thereamong. In addition, by way of example, the radiation detectors are positioned, with respect to the sample, in a direction parallel to and/or a direction perpendicular to the planes of polarization of the LCS photon beams with which the sample is irradiated.

When exciting a certain nuclear level of the isotope of interest within a sample, the levels of other nuclides and isotopes sometimes exist in close proximity thereto. In such cases, as a plurality of NRF gamma rays are generated simultaneously, they may sometimes be indistinguishable in an energy spectrum. As a method of dealing with such cases, a method has been invented wherein the emission directions of NRF gamma rays are controlled by switching the planes of polarization of LCS photon beams, and wherein the NRF gamma ray of interest is detected with high precision by emitting each of the NRF gamma rays in an anticipated direction.

Specifically, the LCS photon beams with which the sample is irradiated are polarized, and the radiation detectors are positioned in certain angular directions relative to their planes of polarization. Although NRF gamma rays are emitted from the sample, each is emitted in a certain direction relative to the plane of polarization of the LCS photons in accordance with the type of transition. Thus, an energy spectrum may be measured with high efficiency and high precision using a plurality of radiation detectors with respect to NRF gamma rays emitted from a plurality of isotope and nuclear levels whose energy levels are in close proximity to one another. In addition, since radiation detectors with high energy resolution ordinarily have a slow response, the upper limit for count rates applicable to measurement is low. However, by using the present method, highly precise measurements are possible even when detectors with low energy resolution are used, and it is thus possible to accommodate high count rate measurements. In other words, by dispersing the emission directions of the NRF gamma rays emitted from the nuclear levels of the isotopes within the sample in a dependent manner with respect to the planes of polarization of the photon beams with which the sample is irradiated, it is possible to lower the count rate per radiation detector.

Effects of the Invention

With the present invention, isotope identification imaging of nuclear fuel materials or explosives concealed within drums or containers in which nuclear reactor fuel or radioactive waste is sealed can be realized while ensuring high precision, high reliability and safety.

BRIEF DESCRIPTION OF THE DRAWINGS

FIGS. 8(a) and (b) are diagrams illustrating methods of arranging detectors and a sample.

MODES FOR CARRYING OUT THE INVENTION

Embodiments of the present invention are described below with reference to the drawings.

Figure 5:
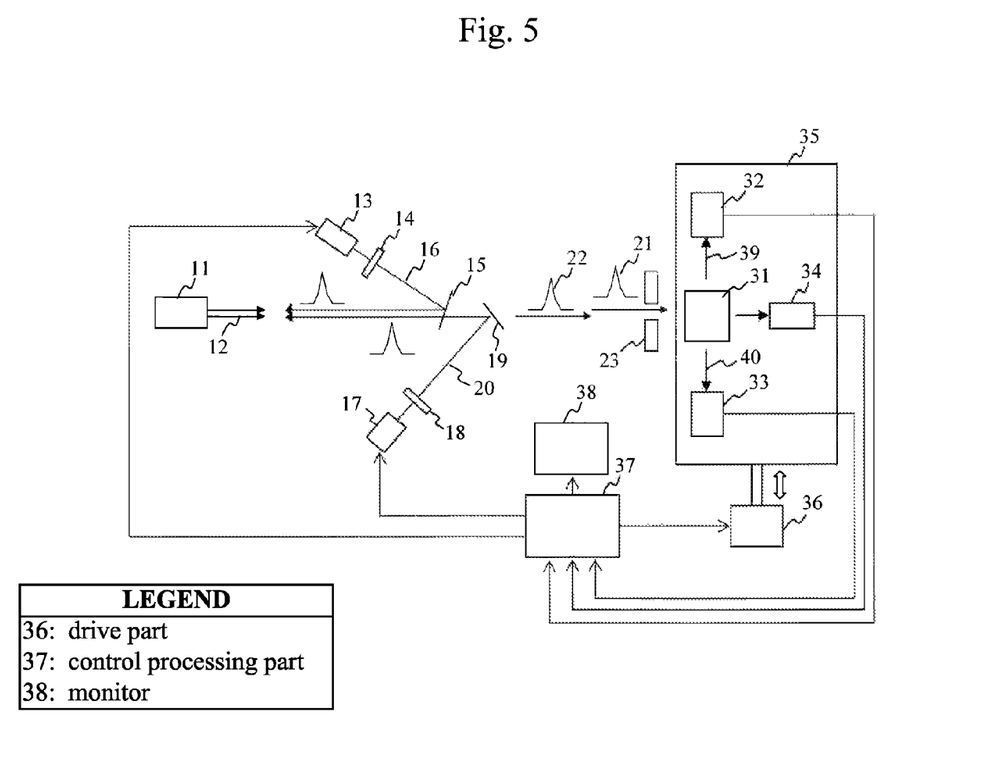
FIG. 5 is a schematic view of a nondestructive inspection system according to the present invention.

FIG. 5 is a schematic view showing a system configuration example for practicing a nondestructive inspection method according to the present invention. This system identifies isotopes within a sample by NRF using LCS photons, and images and displays the spatial distribution thereof.

A nondestructive inspection device of the present embodiment comprises, as an LCS photon beam irradiation part, an electron beam accelerator 11, laser light sources 13 and 17, a collimator 23, radiation detectors 32 and 33 that detect NRF gamma rays generated from a sample, and a photon intensity monitor 34 for monitoring the intensity of photon beams that have penetrated the sample. A sample 31 is positioned on a movable plate 35. By moving the movable plate 35 two-dimensionally in directions parallel to the plane of the paper and in directions perpendicular to the plane of the paper by means of a drive part 36, it is made possible to scan the sample 31 two-dimensionally with respect to the LCS photon beams with which it is irradiated. The laser light sources 13 and 17, and the drive part 36 are controlled by a control processing part 37. The outputs of the radiation detectors 32 and 33, and of the photon intensity monitor 34 are processed at the control processing part 37 to detect, with respect to each move position of the movable plate 35, the abundance of a single or a plurality of isotopes of interest in the sample 31, while at the same time quantifying the abundance ratio thereof to image a spatial distribution and display it on the screen of a monitor 38. The radiation detectors 32 and 33, and the photon intensity monitor 34 may be placed on the movable plate 35. FIG. 5 shows such a case.

With respect to an electron beam 12 of a predetermined energy generated from the electron beam accelerator 11, laser light 16 and 20 of the same wavelength or of a plurality of types of distinct wavelengths (hereinafter referred to as multiple-wavelength) are generated from the laser light sources 13 and 17. The laser light 16 and 20 have their planes of polarization adjusted by wave plates 14 and 18. By way of example, it is assumed that the laser light 16 is vertically polarized with its electric field vector lying in a direction perpendicular to the plane of the paper, and that the laser light 20 is horizontally polarized with a plane of polarization that lies in a plane that is parallel to the plane of the paper. Instead of being linearly polarized, the plane of polarization of the laser light may be circularly polarized or randomly polarized as well. The polarized laser light 16 and 20 are deflected by mirrors 15 and 19, and are made to collide with the electron beam 12 at angle $\theta_1$ as shown in FIG. 2. For the mirror 15, by using a dielectric multilayer mirror, etc., with a narrow wavelength band, it can be made transparent with respect to the laser light 20, thereby making it possible to make the two laser light 16 and 20 coaxial. Although not described herein, using a focusing optical element, etc., each laser light is focused at a point at which it is made to collide with the electron beam 12, thereby effectively generating an LCS photon beam.

By having the laser light 16 and 20 irradiate the electron beam 12 in a pulsed manner with respectively different time structures, such as pulse frequencies or generation timing, etc., pulsed LCS photon beams 21 and 22 are generated at the same scattering angle of $\theta_2$. The pulsed LCS photon beams 21 and 22 may differ from each other in energy. As will be discussed later, in LCS, the plane of polarization of a laser becomes, as is, the plane of polarization of LCS photons (Equation (6), discussed below). It is thus possible to generate a high-energy photon beam whose polarization may be controlled as desired. The pulsed LCS photon beams 21 and 22 with differing planes of polarization are, after having their energies and spatial distributions shaped by the collimator 23, made to irradiate the sample 31, thereby generating NRF gamma rays 39 and 40. It is assumed that only the polarized pulsed LCS photon beam 21 is capable of exciting a reaction that generates the NRF gamma ray 39 of interest of an isotope of interest contained in the sample 31. It is similarly assumed that only the polarized pulsed LCS photon beam 22 is capable of exciting a reaction that generates the NRF gamma ray 40 of interest of another isotope of interest contained in the sample 31. The isotopes may be of different types or of the same type, but the types of transition of the excitation levels must be different. Types of transition are discussed later.

Due to factors stemming from the nuclear structure, the NRF gamma ray 39 is emitted only in the direction of the radiation detector 32, and is detected by the radiation detector 32. In this case, no signal is generated at the radiation detector 33. The NRF gamma ray 40 is emitted only in the direction of the radiation detector 33, and is detected by the radiation detector 33. In this case, no signal is generated at the radiation detector 32. It is noted that the photon intensity monitor 34 should preferably be located at a part of the beam furthest downstream in order to monitor the intensity of the emitted LCS photon beam. By using the photon intensity monitor 34, it is possible to find the absolute values of the intensities of the NRF gamma rays 39 and 40. It is thus possible to quantify the isotope abundance ratio within the sample. It is assumed here that the interaction cross-section and energy of NRF are known.

By simultaneously moving the pulsed LCS photon beams 21 and 22 and the collimator 23 to scan over the sample 31, or by moving the sample 31, it is possible to image the spatial distribution of a plurality of isotopes of interest. In the present embodiment, by driving the movable plate 35, on which the sample 31 is placed, by means of the drive part 36 and relative to the collimator 23, the sample 31 is scanned with the pulsed LCS photon beams 21 and 22. In addition, by appropriately adjusting the power of the laser light sources 13 and 17, it is possible to adjust the intensity of the pulsed LCS photon beams 21 and 22, and to quantify the abundance ratios of a plurality of isotopes contained in the sample 31.

With the present invention, by irradiating the same electron beam with laser light of a single or a plurality of wavelengths, single-wavelength or multiple-wavelength LCS photon beams with aligned beam axes and divergence angles are generated, and a single or a plurality of levels of a single or a plurality of isotopes is/are selectively and simultaneously excited therewith.

In JP 2006-318746 A, there is discussed a method of generating quasi-monochromatic X-rays of 100 keV or below at multiple wavelengths by LCS using a small electron accelerator and pulsed lasers with a plurality of types of distinct wavelengths for use in medical imaging, such as cardiac catheterization, etc. However, an object of the present invention is to generate high energy photon beams in order to quantify, with high precision and in a safe manner, the abundances, spatial distribution, and abundance ratio of isotopes concealed in a strictly shielded box whose maximum iron thickness may measure up to several cm, such as a container, a fuel cladding tube, etc., and to detect them with high efficiency through temporal/spatial discrimination per pulse utilizing the anisotropy of nuclear reactions. It thus differs entirely in concept and methodology.

In addition, it is important that no neutrons be generated due to LCS photon beam irradiation, or that the generated amount thereof be suppressed to a tolerable level. Depending on the isotope, there is a risk that nuclear fission may be triggered due to photonuclear reactions, or a possibility that an isotope within the sample may become a different element through nuclear transmutation. There is also an advantage in that the cost at the time of construction can be reduced significantly by simplifying the shielding required for the measuring system as a whole. Thus, it is preferable that the LCS photon energy be made lower than the neutron emission energy, and that NRF of or below the neutron emission energy be utilized.

With the present invention, by controlling the planes polarization of the emitted lasers, detection sensitivity for a certain level of an isotope of interest is improved. Some nuclear levels are such that NRF gamma rays are emitted in certain directions based on the plane of polarization of the photon beam with which excitation is carried out. By way of example, in electric dipole (E1) transition, magnetic dipole (M1) transition, electric quadrupole (E2) transition, etc., NRF gamma rays are emitted only in directions that are perpendicular or parallel to the electric field or magnetic field, respectively. Thus, by positioning a plurality of photon detectors, each having an appropriate energy resolution and directionality, above, below, to the left of, to the right of, etc., the unit under inspection, and by adjusting the planes of polarization of the excitation photon beams in advance in accordance with the desired level, it is possible to detect the desired NRF gamma rays with sufficient precision and spatial discrimination.

A characteristic of Compton scattering is that the polarization of the photons before and after scattering is preserved. This will be explained by describing the degree of polarization of electromagnetic waves using the Stokes parameters $(a_x, a_y, a_z)$. The direction in which laser light travels is taken to be the z-axis, and the x- and y-axes are so defined as to be perpendicular thereto. The degree of linear polarization of the laser light is denoted $P_1^i$, and is given by Equation (4).

$$P_1^i = a_x^2 - a_y^2 \qquad (4)$$

In the electron rest frame, laser light that has undergone Compton scattering at scattering angle $\theta$, that is, LCS photons, scatters at arbitrary azimuths relative to the rotation about the z-axis. Thus, degree of polarization $P_1^f$ of the LCS photons becomes an average value integrated in all azimuths. This is represented in Equation (5).

$$P_1^f = P_1^i \frac{(1 - \cos\theta)^2}{2\left[\frac{(K_0 - K)^2}{K_0 K} 1 + \cos^2\theta\right]} \qquad (5)$$

Here, $K_0$ and $K$ represent the energies of the laser and LCS photons in the electron rest frame. When expressed in the laboratory frame, Equation (5) would resemble Equation (6).

$$P_1^f = P_1^i \frac{\left(1 - \frac{1 - \rho(1+a)}{1 - \rho(1-\alpha)}\right)^2}{2\left[\frac{\rho^2(1-a)^2}{1 - \rho(1-a)} + 1 + \left(\frac{1 - \rho(1+a)}{1 - \rho(1-a)}\right)^2\right]} \qquad (6)$$

Here, it is assumed that $K_f$ and $K_{f\_max}$ are the energy and the maximum energy of the LCS photons in the laboratory frame, and that ρ is the ratio thereof as follows:

$$\rho = \frac{K_f}{K_{f\_max}} \quad (7)$$

a represents the degree of energy multiplication of the laser light with respect to the maximum energy of the LCS photons, and is given by Equation (8).

$$a = \frac{K_{f\_max}}{4\gamma^2 K_i} \quad (8)$$

The degree of polarization of the LCS photons becomes extremely close to 1 when θ is close to 180 degrees, that is, in the vicinity of ρ=1. Thus, it can be seen that, in LCS, the polarization of the laser light is preserved in the LCS photons, and that a degree of polarization of 100% can be attained near the center of the beam axis. In "Observation of M1 Resonance in $^{206}$Pb Using a Highly Linear Polarized Photon Beam", NUCLEAR PHYSICS A649, pp. 73c-76c, 1999, this method is used to verify the fact that the level of lead-206 with unknown parity is M1.

An object of the present invention is to detect isotopes and measure abundance ratios accurately by focusing on sufficiently reliable isotope levels listed in nuclear data tables, etc., and selectively exciting them. The present invention is of practical importance in that, even in cases where an unknown element is present in a sample of interest and where the level of that element is in proximity to the isotope of interest, so long as the parities, quantum numbers, etc., are different, they can be discriminated with sufficient precision. Specifically, by positioning detectors in directions in which NRF gamma rays are emitted, and by controlling the planes of polarization of the LCS photons, it is possible to, with high reliability, identify isotopes, quantify abundance ratios, and perform imaging thereof even if an isotope whose level is in proximity is present. The present invention differs from conventional methods in that an object thereof is to improve detection accuracy dramatically.

Thus, in transporting nuclear fuel materials, it becomes possible to detect, from outside of a container and in a non-destructive, remote, and safe manner, fissionable materials or nuclear fuel materials, such as uranium, etc., explosives and substances from which they are made, or any other substance besides hydrogen concealed inside the container, and to measure the spatial distribution of isotope nuclei with high spatial resolution. Such objects as strictly restricting and managing the transport of nuclear materials, and a safe and secure society can thus be achieved by preventing terrorism, etc., involving explosives. In addition, it becomes possible to non-destructively and remotely inspect fissionable materials and various isotopes contained in fuel rods and radioactive waste that are handled in nuclear fuel cycles for nuclear power generation, and to visualize the spatial distribution thereof with high precision, thereby making it possible to attain a safe and efficient nuclear fuel cycle.

EXAMPLES

Looking at the chemical formulae for typical industrial and military-use explosive substances used in the world today, it can be seen that most explosives contain carbon, oxygen and nitrogen, and that the proportion of carbon, oxygen and nitrogen varies depending on the explosive.

Figure 6:
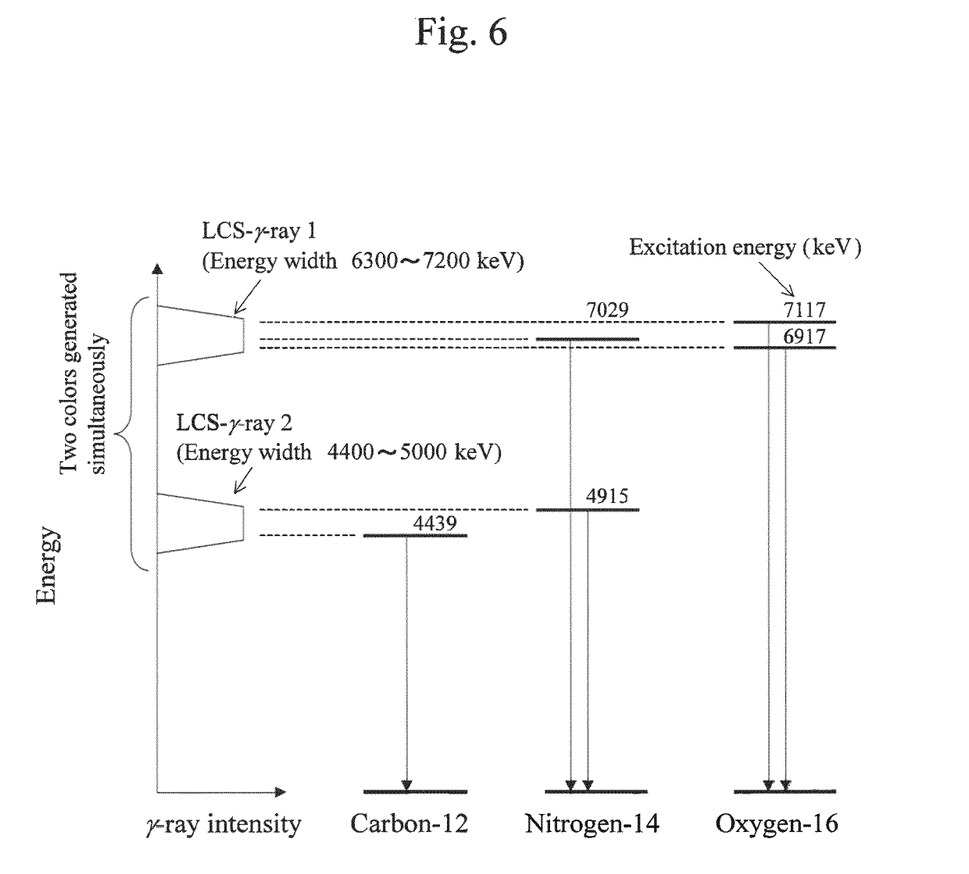
FIG. 6 is a diagram showing the excitation levels of elements ($^{12}C$, $^{14}N$, $^{16}O$) used in the detection of explosives.
Figure 7:
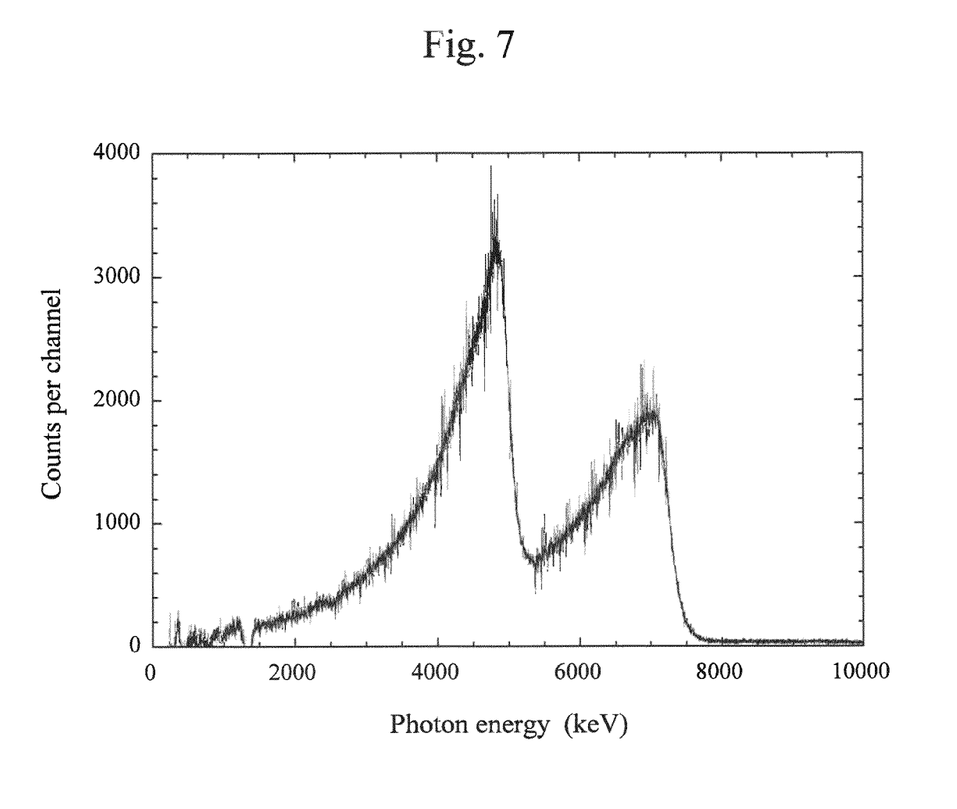
FIG. 7 is a chart showing an energy spectrum of two-wavelength LCS photon beams.

The excitation levels of elements ($^{12}$C, $^{14}$N, $^{16}$O) used in the detection of explosives are shown in FIG. 6. In the present example, carbon-12, oxygen-16 and nitrogen-14 are detected using two-wavelength LCS photon beams, and the abundance ratio thereof is measured. The excitation levels 6917 keV and 7117 keV of oxygen-16, 4915 keV and 7029 keV of nitrogen-14, and 4439 keV of carbon-12 are looked at. Here, by irradiating electrons of an energy of 641 MeV with lasers of wavelengths 1064 nm and 1550 nm, LCS photons of two different energies, namely 7250 keV and 5000 keV (energy spread approximately 12%), are generated, thereby exciting all of these levels. An energy spectrum of two-wavelength LCS photon beams generated by such a method is shown in FIG. 7.

Since LCS photon beams are generated in the travel direction of the electron beam at divergence angles determined by the electron beam, so long as they share the same electron beam, LCS photon beams of differing wavelengths would also be generated along the same axis, and their properties as beams would generally be the same. For the laser with a 1064 nm wavelength, a Nd:YAG or Nd:YVO$_4$ laser is used, and for the laser with a 1550 nm wavelength, a pulsed fiber laser doped with Er is used. It is thus possible to generate the desired two-wavelength LCS photon beams along the same beam axis, and to detect the NRF gamma rays of the respective isotopes. It is noted that, for the lasers, it is also possible to use an appropriately mixed second harmonic, third harmonic, or a higher harmonic or fundamental wave.

Figure 8:
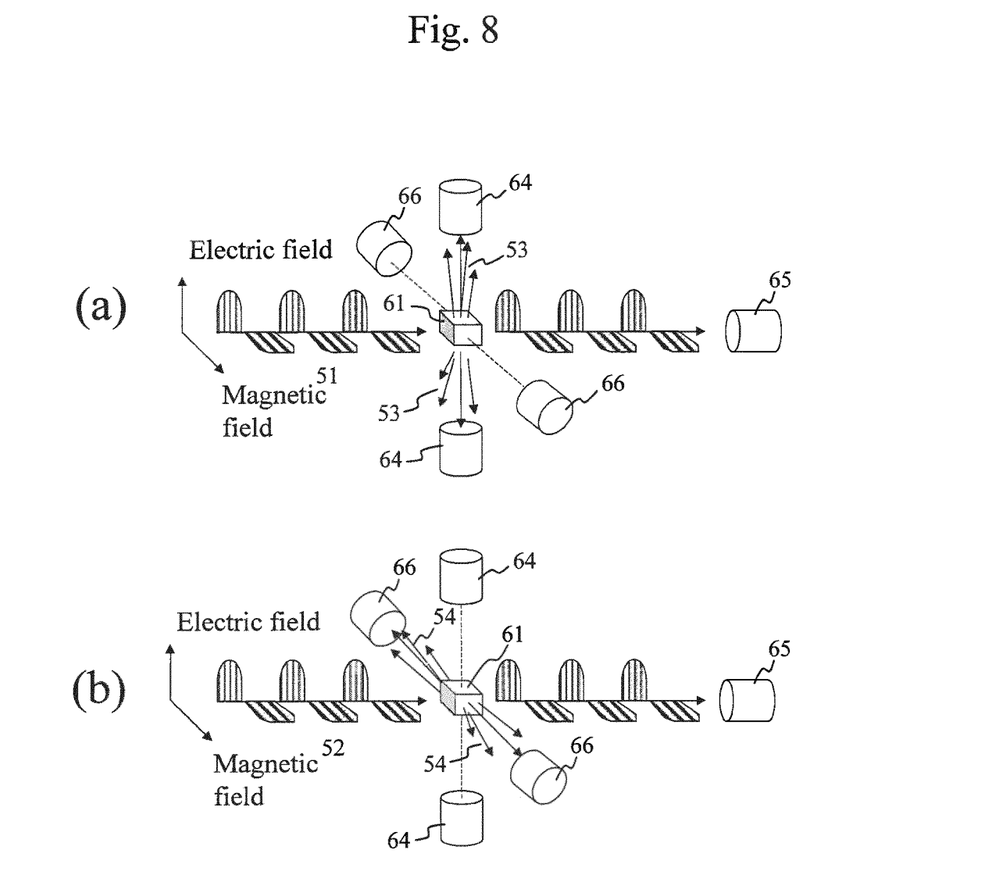

The lasers are all perpendicularly polarized. As shown in FIG. 8, the radiation detectors are positioned above, below, to the left and to the right, that is, in directions perpendicular to and in directions parallel to the planes of polarization of the laser light used to generate LCS photon beams 51 and 52.

If the laser light used to generate the LCS photons are linearly polarized, the LCS photon beams 51 and 52 would also be linearly polarized. The NRF gamma rays 53 of 4439 keV of carbon-12, of 6917 keV of oxygen-16, and of 7029 keV of nitrogen-14 are detected by the radiation detectors 64 above and below as shown in FIG. 8(a), while the NRF gamma rays 54 of 4915 keV of nitrogen-14 and of 7117 keV of oxygen-16 are detected by the radiation detectors 66 to the left and right as shown in FIG. 8(b). The respective NRF gamma rays 53 and 54 are generated with different laser pulses, and have temporally distinct structures.

With respect to the radiation detectors, an energy resolution of 100 keV or below would be sufficient. The energy resolution of high-purity germanium detectors is approximately 10 keV at 5000 keV, which is sufficient for the present measurements. The intensity of the emitted LCS photon beam is measured by a photon intensity monitor 65 positioned behind a sample 61, but in order to improve measurement precision, it is synchronized with the laser pulse to reduce the influence of background radiation, etc.

In the case above, it is, naturally, possible to omit either the radiation detectors 64 or 66 by switching the planes of polarization of the LCS photon beams to a perpendicular or horizontal direction.

The isotope abundance ratios of carbon-12, oxygen-16 and nitrogen-14 are 98.89%, 99.762% and 99.634%, respectively. Thus, their respective abundance ratios may be measured based substantially on NRF gamma ray intensity ratios.

Figure 9:
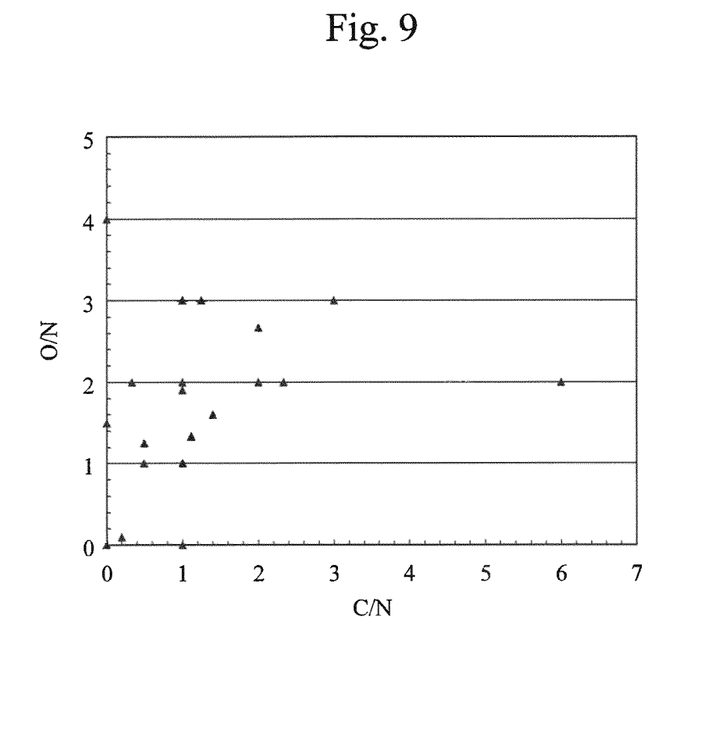
FIG. 9 is a chart showing composition ratios of typical explosives.

Various explosives, carbon-to-nitrogen ratios (C/N), and oxygen-to-nitrogen ratios (O/N) are shown in FIG. 9. Through application of the present invention, it is possible to identify an explosive's type. It is noted that, through application of the present invention, it is possible to detect not only explosives, but also any kind of substance concealed in a container, etc., such as radioactive waste, nuclear fuel, banned drugs or substances from which they are made, etc.

Figure 10:
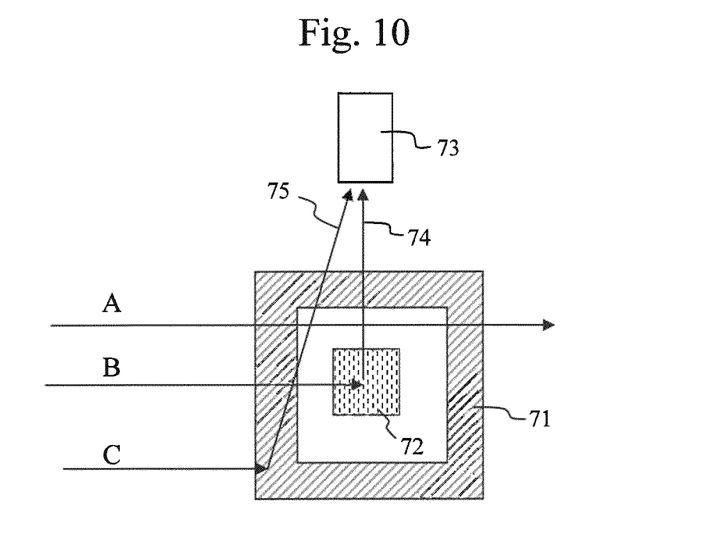
FIG. 10 is a diagram showing how a concealed object is detected according to the present invention.

FIG. 10 is a diagram showing a concealed object being detected according to the present invention. It is now assumed that isotopes of a given nucleus are inside a thick shield box 71 made of iron as a concealed object 72. LCS photon beams are emitted theretowards. LCS photon beam A penetrates the shield box 71 without causing any interaction. LCS photon beam B causes NRF at the concealed object (isotopes of a nucleus) within the shield box, and an NRF gamma ray 74 thereof undergoes height discrimination at a detector 73. Another LCS photon beam, C, causes NRF at the shield box 71, and an NRF gamma ray 75 thereof also undergoes height discrimination at the detector 73. Since the NRF gamma ray 75 is NRF from a constituent element of the shield box, it has an energy that differs from that of the NRF gamma ray 74. Thus, the two are readily discernible using a pulse-height discrimination method.

Figure 11:
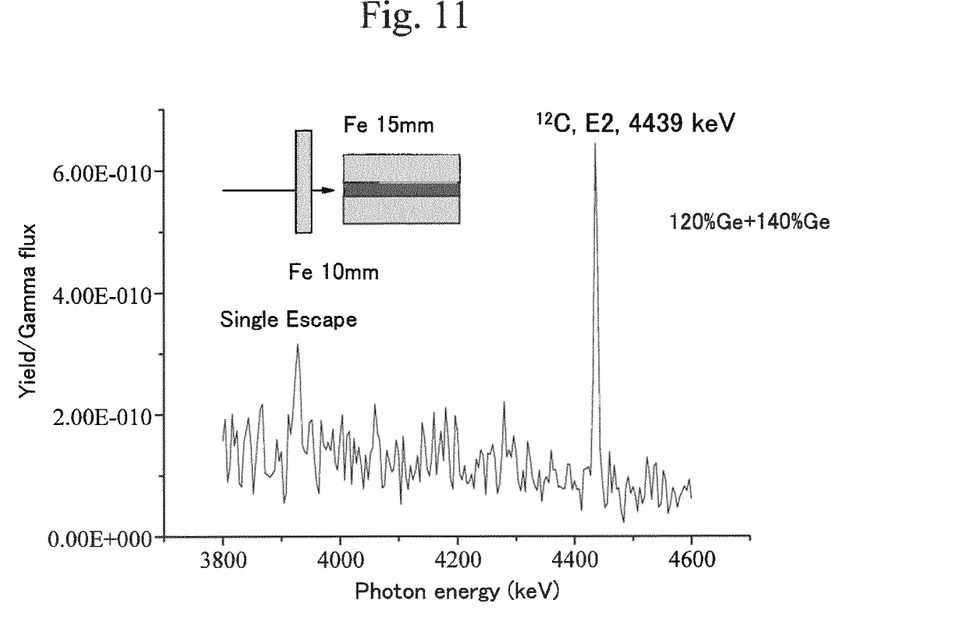
FIG. 11 is a chart where an NRF gamma ray energy spectrum of a concealed object (carbon-12) inside a shield box is measured.

Using an excitation level that is at 4439 keV of carbon-12, which is a type of carbon isotope, experiments to verify the present method were attempted. A carbon isotope (carbon-12) is concealed in an iron box that is 1.5 cm thick. A horizontally polarized LCS photon beam with an energy of 4.6 MeV is emitted theretowards from the outside. The energy of the electron beam and the wavelength (polarization direction) of the laser light in this case are 510 MeV and 1064 nm (horizontal), respectively. The scattering directions of the NRF gamma rays were cut out with an angle spread of approximately 330 microradians about the 180-degree direction. The energy spread resulting therefrom is approximately 4.3% full width at half maximum. Since it is known that the 4439 keV level of carbon-12 undergoes an E2 transition, NRF gamma rays are emitted in directions parallel to the planes of polarization of the LCS photon beams. FIG. 11 is an energy spectrum of NRF gamma rays of 4439 keV of carbon-12 as measured by a high-purity germanium detector positioned in the horizontal direction. As can be seen therein, a clear peak was observed at 4439 keV.

Figure 12:
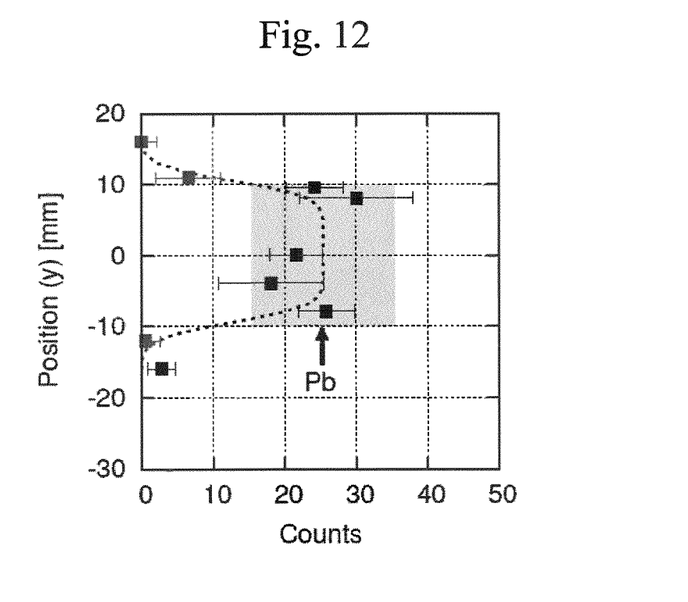
FIG. 12 is a chart showing an example in which the spatial distribution of a concealed object (lead-208) inside a shield box is measured.

Based on the experiment above, results of isotope imaging measurements using NRF gamma rays are shown in FIG. 12. The shield box shown in FIG. 10 containing the concealed object was placed on the movable plate of the nondestructive inspection system described in connection with FIG. 5, and the shield box was linearly scanned with LCS photon beams. A heavy element was selected for the concealed object to simulate a nuclear material, Pb-208, which is an isotope of lead, was used, and 5512 keV was used as the excitation level. It is known that this level undergoes an E1 transition, and NRF gamma rays are emitted in directions perpendicular to the planes of polarization of the LCS photons. Radiation detectors were therefore placed in the horizontal direction, while the planes of polarization of the LCS photon beams were made to be in the perpendicular direction.

Pb-208 was concealed in an iron box with a thickness of 1.5 cm, and perpendicularly polarized LCS photon beams with an energy of 5.7 MeV were emitted. The energy of the electron beam, and the wavelength and plane of polarization of the laser light in this case were 570 MeV, 1064 nm, and in the perpendicular direction, respectively. The scattering directions of the NRF gamma rays were cut out with an angle spread of approximately 330 microradians about the 180-degree direction. The energy spread resulting therefrom is approximately 7% full width at half maximum.

High-purity germanium detectors were used for the radiation detectors, and after the energy spectrum was measured for approximately 30 minutes, the sample on the movable plate was moved in the up/down direction. At the position to which it was moved, an energy spectrum measurement was performed again, and by repeating the above, the correlation was measured between NRF gamma ray count of 5512 keV and sample position. The diameter of the LCS photon beams is 3 mm at the sample position. As can be seen from FIG. 12, NRF gamma rays of the lead isotope Pb-208 were strongly detected within the range of ±10 mm from the reference position. The spatial distribution of the concealed object was thus successfully imaged one dimensionally using the NRF gamma rays of the lead isotope Pb-208 concealed in an iron box with a thickness of 15 mm.

High-purity germanium detectors cannot be used at high count rates, and the maximum count rate is approximately 10 kHz or below. In cases of high count rates, that is, where the NRF gamma ray intensity is high, measurements cannot be made with high precision.

Shortening the duration of inspection by employing high count rate gamma ray detectors is important. By way of example, a case is considered where a screening inspection for dangerous objects with respect to 10 m long shipping containers is to be performed on all containers unloaded at a port. According to Roger Bostelman, "Requirements: Cargo Container Transfer Requirements for the Mobile Offshore Base", Intelligent Systems Division, National Institute of Standards and Technology, 1998, assuming the per-hour throughput of a container crane is approximately 30 containers/hour, the container movement speed during inspection would be approximately 10 cm/s. Further, according to Brian Lewis, "PORT SECURITY: CONTAINER INSPECTION TECHNOLOGY, 2002 Technical Report", The Logistics Institute, Georgia Institute of Technology, 2002, it is stated that the maximum inspection speed with respect to container-transporting trucks for ground transportation is 4-5 miles/h. Accordingly, an inspection speed of approximately several tens of cm/s, and up to 200 cm/s, would be required.

If screening in which LCS photon beams with a diameter of 1 mm are emitted every 1 cm were to be performed, the irradiation time per point would be 0.005 to 0.1 seconds. While a detailed study is described in Non-Patent Document 2, by using LCS photon beams of an intensity that is currently technically feasible to a sufficient extent, isotope identification can be performed in 0.1 seconds or less, and it is thus apparent that the present invention is applicable to the inspection of freight containers. Since the maximum count rate anticipated in such cases is 10 kHz or greater, high-purity germanium detectors cannot be used.

However, the present invention allows for the use of a scintillation detector that uses the inorganic scintillation material $LaBr_3(Ce)$, which accommodates count rates that are up to approximately three figures greater than high-purity germanium detectors (10 MHz). The energy resolution is 1 to 3%, which is 1/10 or less of that of high-purity germanium detectors, but is sufficient for identifying explosives.

Since the planes of polarization of the LCS photon beams preserve the planes of polarization of the incident lasers as is, it is possible to control the directions in which NRF gamma rays are emitted. Consequently, the measurement precision, inspection throughput, and cost performance are improved. Specifically, by scattering NRF gamma rays with close energy levels in different directions in accordance with the difference in the planes of polarization, it is possible to construct an inspection system with which sufficiently high precision and inspection throughput may be attained even when cheap detectors with low energy resolution, such as scintillators, etc., are used.

Nondestructive inspection according to the present invention may, in practice, be performed by being divided into first-stage screening and second-stage inspection. The former refers to measuring the abundance ratios of key elements (e.g., carbon/nitrogen, oxygen/nitrogen, uranium/thorium, etc.) by irradiating one spot or several spots with LCS photon beams, and the likelihood of it being a dangerous explosive or nuclear material is determined in a short period of time. In the latter, imaging inspection with more detailed isotope identification is performed through beam scanning.

Next, an example in which first-stage screening and second-stage inspection are performed is described. In the present example, too, LCS photon beams of several energies are generated along the same beam axis, and the isotope abundance ratios of such elements as carbon, nitrogen, oxygen, etc., are measured by NRF. Further, precision was improved with respect to the discrimination method for the NRF gamma rays thereof. As for the device configuration of the nondestructive inspection system, that shown in FIG. 5 was used. For the radiation detectors 32 and 33, scintillation detectors having a count rate of 10 kHz or above were used although their energy resolution of 1 to 3% is inferior to high-purity germanium detectors.

The device shown in FIG. 5 may be used for both the first-stage screening and the second-stage inspection. However, it is assumed that, in the first-stage screening, the sample 31 is irradiated with LCS photon beams in a relatively coarse manner, such as at predetermined intervals, etc., and that two-dimensionally scanning the LCS photon beams with which the sample 31 is irradiated is only performed in the second-stage inspection. In the second-stage inspection, the outputs of the radiation detectors 32 and 33, and of the photon beam intensity monitor 34 are processed at the control processing part 37, and with respect to each move position of the movable plate 35, the abundances of the plurality of isotope nuclei of interest within the sample 31 are detected, while at the same time the abundance ratios thereof are quantified to image the spatial distribution and display it on the screen of the monitor 38.

With respect to the electron beam 12 of a predetermined energy generated from the electron beam accelerator 11, laser light 16 and 20 are generated from the laser light sources 13 and 17. The planes of polarization of the laser light 16 and 20 are adjusted by the wave plates 14 and 18. This may be attained readily by inserting, taking out or rotating a ½ wave plate. The planes of polarization are determined in accordance with the constituent elements of the object to be inspected or with the type of isotope to be inspected.

The polarized laser light 16 and 20 are respectively deflected by the mirrors 15 and 19, and are made to collide with the electron beam 12 at angle $\theta_1$ as in FIG. 2. Here, in order to maximize photon energy, $\theta_1$ was defined to be 180 degrees. As discussed above, by using a dielectric multilayer mirror, etc., with a narrow wavelength band for the mirror 15, it is possible to coaxially irradiate the electron beam with the two laser light 16 and 20. As a result, it is possible to, without altering the properties of the electron beam at all, generate LCS photon beams with two types of energies by irradiating the same electron beam with lasers of two types of wavelengths. The intensity of each laser light is adjusted as deemed appropriate depending on the reaction cross-section (likelihood of interaction) of the isotope to be measured. It is preferable that it be so adjusted that the intensity of the emitted NRF gamma ray would generally have a variation of within approximately several tens of %.

The laser light 16 and 20 generate the pulsed LCS photon beams 21 and 22 by irradiating the electron beam 12 in a pulsed manner with respectively different time structures, such as pulse frequencies or generation timing, etc. The pulsed LCS photon beams 21 and 22 may respectively differ in energy, or they may differ in terms of their planes of polarization, or they may differ in both.

The pulsed LCS photon beams 21 and 22 with differing planes of polarization pass through the collimator 23, after which they irradiate the sample 31, and the NRF gamma rays 39 and 40 are generated. When the position and direction of the electron beam do not change, there is no need to adjust the collimator 23. In the present example, since the adjustment of the LCS photon beam energy is performed solely by way of the lasers, position adjustment of the collimator need only be performed once before starting measurement, and no subsequent adjustment is required at all. By utilizing LCS, it is possible to generate LCS photon beams with an energy spread of approximately 0.1 to 20% at high intensities.

It is assumed that only the polarized pulsed LCS photon beam 21 is capable of exciting a reaction that generates the NRF gamma ray 39 of interest of an isotope of interest contained in the sample 31. It is similarly assumed that only the polarized LCS photon pulsed beam 22 is capable of exciting a reaction that generates the NRF gamma ray 40 of interest of another isotope of interest contained in the sample 31. The isotopes may be of different types or of the same type, but the types of transition of the excitation levels must be different.

The NRF gamma ray 39 is emitted only in the direction of the radiation detector 32, and is detected by the radiation detector 32. In this case, no signal is generated at the radiation detector 33. The NRF gamma ray 40 is emitted only in the direction of the radiation detector 33, and is detected by the radiation detector 33. In this case, no signal is generated at the radiation detector 32. In addition, by using the photon intensity monitor 34 located at a part of the beam furthest downstream, it is possible to find the absolute values of the intensities of the NRF gamma rays 39 and 40. It is thus possible to quantify the isotope abundance ratio within the sample.

The NRF gamma ray energies (keV) and transition models of carbon-12, nitrogen-14, and oxygen-16 used for the detection of explosives are shown in Table 1.

TABLE 1

| Element | Energy | Transition model |
| --- | --- | --- |
| Carbon-12 | 4439 | E2 |
| Nitrogen-14 | 7029 | M1 |
|  | 4915 | E1 |
| Oxygen-16 | 6917 | E2 |
|  | 7117 | E1 |

In Table 1, the symbols E1, M1, E2, etc., represent transition models of nuclei, where E1 signifies that NRF gamma rays are emitted in a direction perpendicular to the plane of polarization of the photon beam, and E2 and M1 signify that NRF gamma rays are emitted in a parallel direction.

The excitation levels of the elements provided above are broadly in the ranges of 4.4 to 5 MeV, and 6.9 to 7.1 MeV. Thus, by generating two-wavelength LCS photon beams of 7.25 MeV and 5 MeV (energy spread approximately 20%) along the same axis and observing the respective NRF gamma rays of the isotopes, it is possible to measure elemental ratios. By finding the above-mentioned elemental ratios, it is possible to identify the explosive's type. By finding the abundances, it is possible to find the amount.

With respect to detecting specific isotopes (e.g., carbon-12, nitrogen-14, etc.), the energy of the electron beam by the electron accelerator, the wavelength from the laser sources, laser polarization by the wave plates, and the radiation detectors are, by way of example, combined in the following manner.

Electron energy: 641 MeV
Laser polarization: Vertical
4439 keV of $^{12}$C (E2) (laser: wavelength 1550 nm, detector: perpendicular direction)
4915 keV of $^{14}$N (E1) (laser: wavelength 1550 nm, detector: horizontal direction)
6917 keV of $^{16}$O (E2) (laser: wavelength 1064 nm, detector: perpendicular direction)
7029 keV of $^{14}$N (M1) (laser: wavelength 1064 nm, detector: perpendicular direction)
7117 keV of $^{16}$O (E1) (laser: wavelength 1064 nm, detector: horizontal direction)

It is thus possible to identify the five NRF levels (three nuclides) above.

Alternatively, by combining the energy of the electron beam, wavelength from the laser sources, the laser polarization by the wave plates, and the radiation detectors as follows, it is possible to identify two NRF levels (two nuclides).

Electron energy: 530 MeV
Laser polarization: Vertical
4439 keV of $^{12}$C (E2) (laser: wavelength 1064 nm, detector: perpendicular direction)
4915 keV of $^{14}$N (E1) (laser: wavelength 1064 nm, detector: horizontal direction)

LIST OF REFERENCE NUMERALS

1 Photon beam
2 Sample
3 Isotope
4 NRF gamma ray
5 Scatter X-ray
6 High energy resolution radiation detector
7 Photon intensity monitor
11 Electron beam accelerator
12 Electron beam
13 Laser light source
14 Wave plate
15 Mirror
16 Laser light
17 Laser light source
18 Wave plate
19 Mirror
20 Laser light
21 Pulsed LCS photon beam
22 Pulsed LCS photon beam
23 Collimator
31 Sample
32 Radiation detector
33 Radiation detector
34 Photon intensity monitor
35 Movable plate
36 Drive part
37 Control processing part
38 Monitor
51 LCS photon beam
52 LCS photon beam
53 NRF gamma ray
54 NRF gamma ray
61 Sample
64 Radiation detector
65 Photon intensity monitor
66 Radiation detector
71 Shield box
72 Concealed object
73 Detector
74 NRF gamma ray
75 NRF gamma ray

The invention claimed is:

1. A nondestructive inspection system comprising:
a plate that holds a sample;
a plurality of radiation detectors positioned in predetermined directions relative to the sample held by the plate;
a photon beam irradiation part that irradiates the sample held by the plate with a plurality of types of quasi-monochromatic photon beams having differing energies and whose planes of polarization are each controlled, the quasi-monochromatic photon beams being made to be coaxial;
a drive part that relatively moves the plate and the photon beam irradiation part;
a control processing part that controls the drive part and to which detection signals from the plurality of radiation detectors are inputted; and
a display part;
wherein the plurality of radiation detectors are positioned in directions that allow for detection of nuclear resonance fluorescence (NRF) gamma rays emitted from an isotope within the sample in emission directions that are dependent on the planes of polarization of the plurality of types of quasi-monochromatic photon beams with which the sample is irradiated,
wherein the control processing part identifies an isotope of interest that is present in a quasi-monochromatic photon beam irradiated region in the sample based on the detection signals of the plurality of radiation detectors, and
wherein a spatial distribution of the isotope is visualized and displayed on the display part.

2. The nondestructive inspection system according to claim 1, wherein the photon beam irradiation part comprises:
an electron beam accelerator that generates an electron beam of a predetermined energy;
a first laser light source that generates laser light of a first wavelength and having a first polarization;
a second laser light source that generates laser light of a second wavelength and having a second polarization;
an optical system that causes the laser light of the first wavelength and the laser light of the second wavelength to collide, as coaxial light, with the electron beam at a first angle; and
a collimator that transmits a first polarized photon beam generated in a second angular direction relative to the electron beam due to the collision between the electron beam and the laser light of the first wavelength, and a second polarized photon beam generated in the second angular direction due to the collision between the electron beam and the laser light of the second wavelength.

3. The nondestructive inspection system according to claim 2, wherein the control processing part controls the first laser light source and the second laser light source to generate pulsed light, each with a different time structure, to be generated as the laser light of the first wavelength and the laser light of the second wavelength.

4. The nondestructive inspection system according to claim 1, wherein the plurality of types of quasi-monochromatic photon beams have their energies and planes of polarization defined in such a manner that a plurality of NRF gamma rays are emitted in different directions from a single or a plurality of nuclear levels of a single or a plurality of isotopes in the sample due to irradiation by the photon beams.

5. The nondestructive inspection system according to claim 1, wherein the plurality of radiation detectors are positioned, relative to the sample, in directions parallel to and/or directions perpendicular to the planes of polarization of the plurality of types of quasi-monochromatic photon beams with which the sample is irradiated, or at arbitrary angles.

6. The nondestructive inspection system according to claim 1, further comprising a photon intensity monitor that detects an intensity of the plurality of types of quasi-monochromatic photon beams with which the sample is irradiated.

7. The nondestructive inspection system according to claim 1, wherein the isotope of interest comprises an isotope of an element that forms an explosive, including carbon-12, nitrogen-14, and oxygen-16.

8. The nondestructive inspection system according to claim 1, wherein the energies of the plurality of types of quasi-monochromatic photon beams emitted from the photon beam irradiation part are equal to or less than a neutron emission energy.

9. The nondestructive inspection system according to claim 1, wherein the drive part drives the plate in such a manner that the sample held by the plate is scanned by the plurality of types of quasi-monochromatic photon beams emitted from the photon beam irradiation part.

10. The nondestructive inspection system according to claim 1, wherein the plurality of types of quasi-monochromatic photon beams are laser-Compton scattering (LCS) photon beams generated using a polarization of laser light, and the planes of polarization thereof are selected in accordance with a constituent element of an object to be inspected or with the type of isotope to be inspected.

11. The nondestructive inspection system according to claim 1, wherein the planes of polarization and energies of the plurality of types of quasi-monochromatic photon beams are controlled in such a manner that the NRF gamma rays are emitted in desired directions in accordance with a transition model that is determined by the nuclear structure of an isotope in the sample.

12. The nondestructive inspection system according to claim 1, wherein the plurality of radiation detectors positioned in pre-defined directions to detect the NRF gamma rays utilizing anisotropy of the emission directions of the NRF gamma rays.

13. The nondestructive inspection system according to claim 1, wherein the count rate per radiation detector is lowered by dispersing the emission directions of the NRF gamma rays emitted from a nuclear level of an isotope in the sample in a manner dependent on the planes of polarization of the plurality of types of quasi-monochromatic photon beams with which the sample is irradiated.

14. The nondestructive inspection system according to claim 1, wherein the plurality of radiation detectors positioned in different directions relative to the sample detects the plurality of NRF gamma rays emitted from nuclear levels of the isotopes with close energies.

15. The nondestructive inspection system according to claim 1, wherein the plurality of radiation detectors comprise scintillator detectors.

16. The nondestructive inspection system according to claim 1, wherein the plurality of radiation detectors are structured to detect the NRF gamma rays of or below a neutron generation threshold.

17. The nondestructive inspection system according to claim 1, wherein the photon beam irradiation part comprises:
  an electron beam accelerator that generates an electron beam of a predetermined energy;
  a plurality of laser light sources; and
  a collimator extracting a plurality of polarized LCS photon beams generated, due to the collision, in a second angular direction, wherein
  two or more types of polarized laser light with differing wavelengths generated from the plurality of laser light sources are made to collide, as coaxial light, with the electron beam at a first angle.

18. The nondestructive inspection system according to claim 17, wherein the plurality of laser light sources are configured to provide adjustment of the energies of the polarized LCS photon beams.

19. The nondestructive inspection system according to claim 17, wherein the collimator is configured to be adjustable in position, thus enabling position adjustment of the collimator before starting measurement.

* * * * *